United States Patent [19]

Brown et al.

[11] Patent Number: 5,249,672

[45] Date of Patent: Oct. 5, 1993

[54] MULTIPLE SUTURE RETAINER

[75] Inventors: David L. Brown, Wallingford; Stanley J. Malinowski, Guilford; Hans-Jurgen F. Sinn, Fairfield, all of Conn.

[73] Assignee: United States Surgical Corporation, Norwalk, Conn.

[21] Appl. No.: 834,695

[22] Filed: Feb. 11, 1992

[51] Int. Cl.[5] .................. B65D 85/24; A61B 17/06
[52] U.S. Cl. .................. 206/63.3; 206/380; 206/388; 206/482
[58] Field of Search .............. 206/63.3, 63.5, 227, 206/380, 388, 477–483, 486, 487; 53/449, 459

[56] References Cited

U.S. PATENT DOCUMENTS

| 1,585,498 | 5/1926 | Kenyon . | |
|---|---|---|---|
| 1,598,101 | 8/1926 | Newman | 206/388 |
| 2,617,523 | 11/1952 | Zoller . | |
| 2,692,676 | 10/1954 | Grover . | |
| 3,136,418 | 6/1964 | Stacy et al. . | |
| 3,206,018 | 9/1965 | Lewis | 206/633 |
| 3,280,971 | 10/1966 | Regan, Jr. . | |
| 3,363,751 | 1/1968 | Shave et al. . | |
| 3,444,994 | 5/1969 | Kaepernik et al. . | |
| 3,487,917 | 1/1970 | Shave et al. . | |
| 3,627,120 | 12/1971 | Bordeau | 206/388 |
| 3,759,376 | 9/1973 | Lisowski . | |
| 3,819,039 | 6/1974 | Erickson . | |
| 3,857,484 | 12/1974 | Thyen . | |
| 3,876,068 | 4/1975 | Sonnino . | |
| 3,985,227 | 10/1976 | Thyen et al. . | |
| 4,014,434 | 3/1977 | Thyen . | |
| 4,034,850 | 7/1977 | Mandel et al. | 206/227 |
| 4,089,409 | 5/1978 | Cerwin . | |
| 4,120,395 | 10/1978 | Mandel et al. . | |
| 4,126,221 | 11/1978 | Cerwin . | |
| 4,135,623 | 1/1979 | Thyen . | |
| 4,215,777 | 8/1980 | Strickland . | |
| 4,264,011 | 4/1981 | Dalbo et al. . | |
| 4,391,365 | 7/1983 | Batchelor | 206/380 |
| 4,412,613 | 11/1983 | Kubas . | |
| 4,412,614 | 11/1983 | Ivanov et al. . | |
| 4,421,231 | 12/1983 | McCarn . | |
| 4,491,218 | 1/1985 | Aday . | |
| 4,533,041 | 8/1985 | Aday et al. . | |
| 4,572,363 | 2/1986 | Alpern . | |
| 4,828,108 | 5/1989 | Roth et al. . | |
| 4,884,681 | 12/1989 | Roshdy et al. . | |
| 4,887,710 | 12/1989 | Roshdy et al. . | |
| 4,896,767 | 1/1990 | Pinheiro . | |
| 4,961,498 | 10/1990 | Kalinski et al. . | |
| 4,967,902 | 11/1990 | Sobel et al. . | |

FOREIGN PATENT DOCUMENTS

| 549594 | 12/1957 | Canada . |
|---|---|---|
| 732466 | 4/1966 | Canada . |
| 874699 | 8/1961 | United Kingdom . |
| 1089105 | 11/1967 | United Kingdom . |

Primary Examiner—Jimmy G. Foster

[57] ABSTRACT

A suture package for holding needle suture combinations individually on removable insert strips. The suture package includes three folding panels, two of which releasably hold the insert strips by means of tabs, and one of which is a cover panel. At least one needle-suture combination is mounted on each strip.

17 Claims, 3 Drawing Sheets

MULTIPLE SUTURE RETAINER

BACKGROUND OF THE INVENTION

1. Field of the Invention

This invention relates to a foldable package for retaining multiple sutures.

2. Background of the Art

Packaging of surgical needles and sutures requires that the needles be secured properly to prevent displacement, as well as being simply and quickly removable from their packages for use by the surgeon. Jarring and displacement of such sharp needles will tend to dull their edges and reduce their effectiveness while increasing trauma to the patient during use.

Also, it is desirable to package the needle-suture combinations in a manner where they are sufficiently separated for ready access to the user when they are needed. Moreover, the suture packages must be capable of receiving and holding sutures of various sizes while generally not effecting the quality, shape or strength of the suture in any way.

Various types of suture packages are known. For example, U.S. Pat. No. 4,896,767 to Pinheiro discloses a three-panel suture retaining package possessing two suture mounting panels and one intermediate panel. Plastic foam strips extending across the suture mounting panels are provided with slots for holding a plurality of needle-suture combinations. Each suture mounting panel has a cover flap which folds over to enclose the needle display area.

U.S. Pat. No. 4,572,363 to Alpern discloses a foldable suture retainer for multi-strand sutures providing for single strand delivery of the sutures from the retainer. The retainer has flaps (see items 44, 45, 46 in FIG. 4) which fold over to form separate compartments, each compartment holding a double armed suture (i.e., a suture with a needle at both ends). The needles are held in slits in a foam pad.

U.S. Pat. Nos. 4,533,041 and 4,491,218 to Aday disclose multi-strand suture packages for individually dispensing sutures. The suture packages each have rectangular panels foldably connected to each other for retaining sutures.

U.S. Pat. No. 4,421,231 to McCarn discloses a display and storage package for an elongated flat article, such as a thread and yarn organizer. Individual samples of yarn are wound around flat strips which are stored in elongated pockets. The pockets have inwardly directed projections for retaining the flat strip within the pocket until the end of the flat strip is moved around as end projection.

U.S. Pat. No. 4,391,365 to Batchelor discloses a single dispensing multiple suture package which includes a plurality of cards for separately containing a plurality of sutures. The package possesses a foam strip with slits for holding the armed ends of the sutures.

U.S. Pat. No. 4,135,623 to Thyen discloses a three panel folded construction providing two suture mounting panels. Across its width each suture mounting panel is provided at the upper end with a foam strip having slits for securing the armed ends of the sutures. Each panel can accommodate more than one armed suture.

In general, a most significant objective in suture packaging is to store and maintain the relatively delicate ligatures in some form of spaced relation to each other so that access and removal of the suture may be readily available without adversely affecting the ligature or the needle as noted hereinabove. The present invention is directed to a suture package wherein a plurality of sutures may be stored in a single package while maintaining the individuality of each suture with respect to the others.

SUMMARY OF THE INVENTION

A suture package is provided herein which comprises a plurality of foldable connected panel members including at least one insert holding panel member having means to releasable hold at least one suture holding insert; and at least one suture holding insert slidably mountable to the inserting holding panel member and removable therefrom, the suture holding insert having means to releasably hold an individual needle-suture combination.

The panel members are connected at substantially parallel folding portions defined by perforated fold lines and may include an intermediate strip defined by two perforated fold lines, the intermediate strip having a width sufficient to accommodate the width of the suture package when folded so as to facilitate flat folding of the package.

The panel members can include two contiguous insert holding panels and one cover panel, each insert hold panel being adapted to hold at least two inserts in substantially parallel relationship.

The suture package, when folded, includes an access opening at each of two opposite ends, the suture holding inserts mounted to one of the insert holding panels being slidably removable through a respective one of the openings, and the suture holding inserts mounted to the other of the inset holding panels being slidably removable through the other of the openings.

The cover panel can include a locking tab, and one of the insert holding panels can include a cooperating locking slot for receiving said locking tab.

The suture package includes a plurality of tabs configured, dimensioned, and positioned so as to overlapping engage said insert, each being an elongated strip having a fold-over end portion for covering the needle-suture combination. The inserts have a pair of foam pads fixedly attached at spaced apart locations, each foam pad having means such as slits to releasably engage the needle-suture combination.

The suture package is optionally constructed from a flexible material such as cardboard, or plastic.

The suture package of the present invention is particularly advantageous for very small gauge sutures, such as suture size 7/0 and smaller, because the package allows such delicate sutures to be transferred to the surgical field without undue handling prior to use.

DETAILED DESCRIPTION OF PREFERRED EMBODIMENT(S)

The multiple suture retainer of the present invention provides convenient means to individually dispense removable suture-holding insert strips. Each strip preferably holds a single needle-suture combination, but it is contemplated that each strip may hold more than one needle-suture combination if desired.

Figure 1:
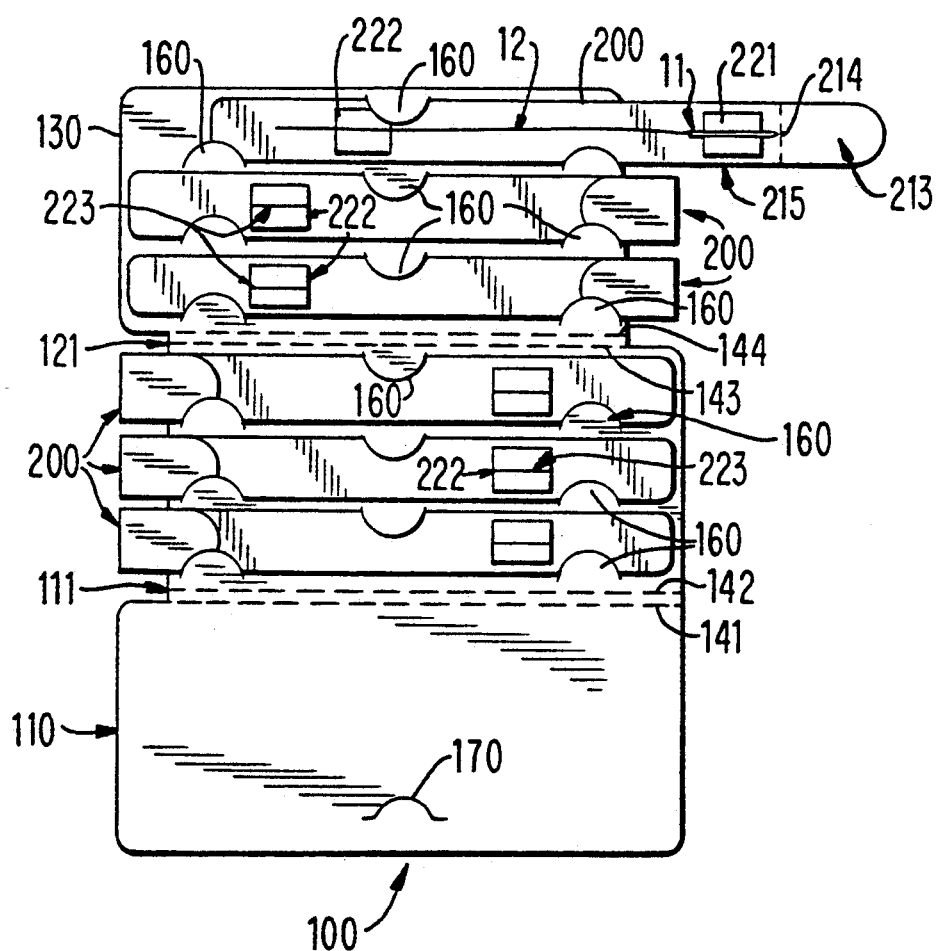
FIG. 1 is a plan view of the opened multiple suture retainer of the present invention.

Referring to FIG. 1, the multiple suture retainer 100 includes three panels 110, 120, and 130, which are connected at perforated fold lines 141, 142, 143, and 144.

Perforations 141 and 142 define a narrow rectangular portion 111 of panel 110; perforations 143 and 144 define a narrow rectangular portion 121 of panel 120. In order to permit flat folding of the retainer, the narrow rectangular portions 111 and 121 are of sufficient width to accommodate the thickness of the panels and the contents of the multiple suture retainer when the retainer 100 is folded. See, for example, FIG. 3, which illustrates a partially folded suture retainer 100. While it is desirable to provide the suture retainer 100 with such narrow strip portions 111 and 121, it is also possible to construct a retainer package with single perforated fold lines at the edges (e.g. lines 141 and 143 only, or lines 142 and 144 only) so as not to define narrow strip portions 111 and 121. Such an alternative will result in a retainer package with a slightly convex shape when folded. It is also acceptable to construct an embodiment in which the fold lines are not perforated.

As can be seen from FIG. 1, panels 120 and 130 are insert holding panels. Panel 110 is a cover panel. The needle-suture combinations are held individually on removable elongated insert strips 200. Each strip 200 comprises an elongated portion 215 and a relatively shorter fold-over flap 213 which is foldably connected to elongated portions 215 at bend line 214. FIG. 1 shows one strip partially removed and with flap 213 opened to display the needle 11. Strips 200 each contain two foam pads for holding the needle-suture combination. Pad 221 is slotted to engage and hold needle 11. The rear pad 222 contains a slit 223 to hold suture 12. The suture 12 is thus extended along strip 200 and securely mounted thereto. The fold-over flap 213 is of such size and configuration to cover and protect the needle 11.

Strips 200 are parallelly mounted to the holding panels by means of strip holding tabs 160, which are formed from arcuate slits cut into the panels. The strips 200 are disposed along the respecting holding panels and underneath the tabs so as to be slidably removable from the suture retainer 100. The strips 200 disposed on panel 130 are pulled and opened in a direction opposite that of the strips 200 on panel 120. Three strips 200 are positioned on each holding panel, although it is contemplated that suture retainer 100 may be adapted to hold more or less than three strips on each holding panel.

Figure 2:
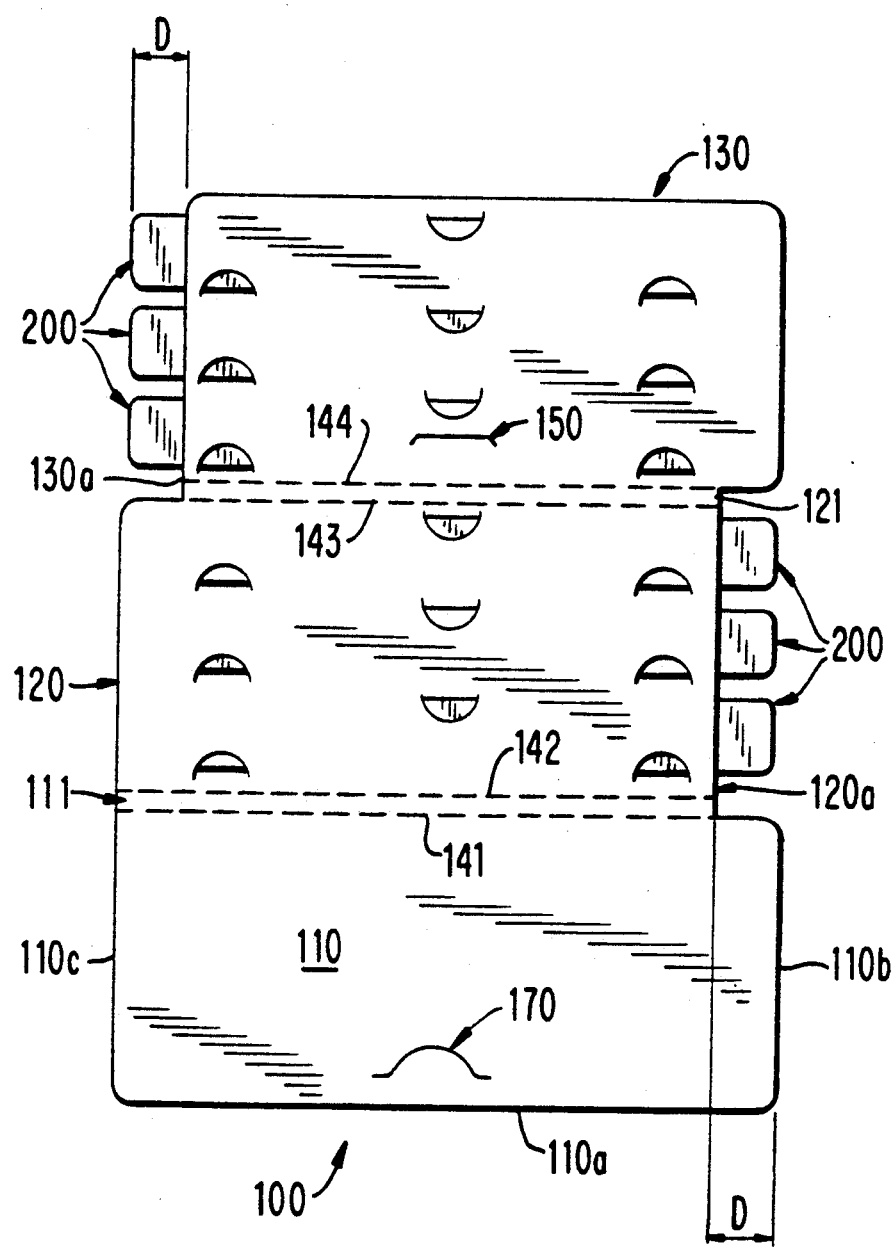
FIG. 2 is a plan view of the opposite side of the opened multiple suture retainer of the present invention.
Figure 3:
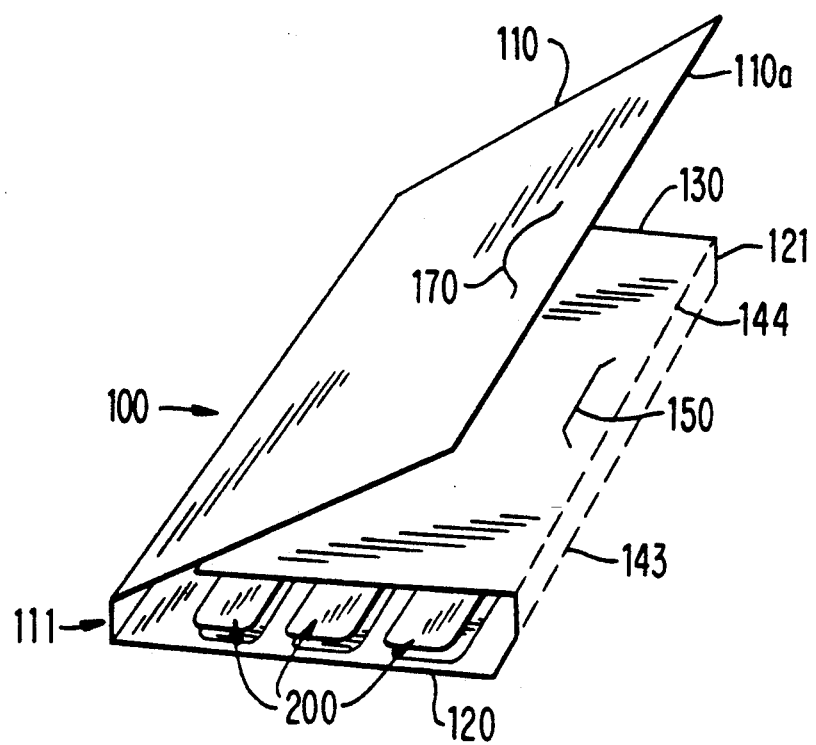
FIG. 3 is a perspective view of the multiple suture retainer in partially folded configuration.

Referring to FIGS. 1, 2, and 3, the cover panel includes locking tab 170 which is adapted to engage locking slot 150 on panel 130. The locking tab 170 faces away from edge 110a of the cover panel.

Insert holding panels 120 and 130 have edges 120a and 130a, respectively, which are indented a distance D from the full length of the suture retainer 100 as defined by the length between edges 110b and 110c. The indentation of panel 120 is on the side opposite that of the indentation of panel 130, and both indentations correspond to the sides toward which the respective insert strips 200 are to be pulled for removal and toward which flaps 213 are oriented for opening. The distance D is sufficient to allow the user to grasp the flap end of the inserts 200 with his fingers and can be, for example, from about ¼ inch to about ¾ inch. The overall dimensions of the multiple suture retainer 100 are such as to permit convenient holding of the suture retainer 100 in the user's hand.

The multiple suture retainer package of the present invention is assembled by loading one or more sutures or needle-suture combinations onto each insert 200, then mounting the inserts 200 onto the appropriate holding panels. The multiple suture retainer 100 is then closed by folding. Referring to FIG. 3, the multiple suture retainer of the present invention is folded by first folding panel 130 over panel 120, and then folding cover panel 110 over panel 130. The locking tab 170 is then inserted into locking slot 150, thereby securing the multiple suture retainer 100 in the folded configuration. In using the multiple suture retainer 100 during a surgical suturing procedure, the surgeon removes an insert 200 from the retainer package, and then removes a suture or needle-suture combination from the insert.

The panels (110, 120, and 130) and insert strips 200 can be constructed from any material having properties suitable for the functions described herein, such as any of the materials currently used for suture retainer packages. One suitable material is cardboard or other type of heavy paper product. Plastic materials may also be used.

What is claimed is:

1. A suture package which comprises:
   a) a plurality of foldably connected panel members including two insert holding panels and one cover panel, said insert holding panels having means to releasably hold at least two suture holding inserts in substantially parallel relationship; and,
   b) at least one suture holding insert mountable to one of said two insert holding panels and adapted to be engaged by said releasably holding means and to be removable therefrom, the suture holding insert having means to releasably hold at least one suture, wherein the suture package when folded, includes an access opening at each of two opposite ends, the suture holding inserts mounted to one of said holding panels being slidably removable through a respective one of said openings, and the suture holding inserts mounted to the other of said insert holding panels being slidably removable through the other of said openings.

2. The suture package of claim 1, wherein said panel members are connected at folding portions defined by perforated fold lines.

3. The suture package of claim 2, wherein said folding portions are substantially parallel to each other.

4. The suture package of claim 2, wherein said folding portions each include an intermediate strip defined by two perforated fold lines, said intermediate strip having a width sufficient to accommodate the width of the suture package when folded so as to facilitate flat folding of the package.

5. The suture package of claim 4, wherein said intermediate strip defined perforated fold lines are parallel to each other.

6. The suture package of claim 1, wherein the insert holding panels are contiguous.

7. The suture package of claim 1, wherein said cover panel includes a locking tab, and one of said insert holding panels includes a locking slot for receiving said locking tab.

8. A suture package which comprises:
   a) a plurality of foldably connected panel members including at least one insert holding panel member having a plurality of tabs configured, dimensioned, and positioned so as to overlappingly engage and releasably hold at least one suture holding insert; and, b) at least one suture holding insert mountable to said insert holding panel member and adapted to be engaged by at least one of said tabs and to be removable therefrom, the suture holding insert having means to releasably hold at least one suture, wherein said suture holding insert is slidably removable from said insert holding panel when said panel members are folded.

9. The suture package of claim 8, wherein said package is constructed from a material selected from the group consisting of cardboard, and plastic.

10. The suture package of claim 8 with at least one suture contained therein.

11. A suture package which comprises:
a) a plurality of foldably connected panel members including at least one insert holding panel member having means to releasably hold at least one suture holding insert; and,
b) at least one suture holding insert mountable to said insert holding panel member and adapted to be engaged by said releasably holding means and to be removable therefrom, the suture holding insert having means to releasably hold at least one suture, wherein said suture holding insert is slidably removable from said insert holding panel when said panel members are folded, wherein said suture is in combination with a needle and said at least one insert is an elongated strip having a fold-over end portion for covering the needle of the needle-suture combination.

12. A suture package which comprises:
a) a plurality of foldably connected panel members including at least one insert holding panel member having means to releasably hold at least one suture holding insert; and,
b) at least one suture holding insert mountable to said insert holding panel member and adapted to be engaged by said releasably holding means and to be removable therefrom, the suture holding insert having means to releasably hold at least one suture, wherein said suture holding insert is slidably removable from said insert holding panel when said panel members are folded and wherein said means to releasably hold the suture comprises a pair of foam pads fixedly attached to the suture holding insert at spaced apart locations, each foam pad having means to releasably engage the suture.

13. The suture package of claim 12, wherein said suture is in combination with a needle, and said means to releasably engage the suture includes a slit in each of said foam pads, one slit being adapted to receive a suture and the other slit being adapted to receive a needle.

14. A suture package, which comprises:
a) foldably connected panels which include two end panels and an intermediate panel therebetween, one of said end panels comprising a cover panel, and said intermediate panel and the other of said panels having means to releasably hold a plurality of suture holding inserts wherein said means to releasably hold a plurality of suture holding inserts comprises a plurality of tabs configured, dimensioned, and positioned so as to overlappingly engage said inserts and releasably hold them in spaced apart substantially parallel orientation; and
b) a plurality of suture holding inserts mounted to each of said insert holding panels and removable therefrom, each suture holding insert having means to releasably hold a suture.

15. The suture package of claim 14, wherein said suture is in combination with a needle, and said means to releasably hold the suture comprises a pair of foam pads fixedly attached to the suture holding insert at spaced apart locations, each foam pad having means to releasably engage the needle-suture combination.

16. The suture package of claim 15, wherein said means to releasably engage the needle-suture combination includes a slit in each of said foam pads, one slit being adapted to receive a suture, and the other slit being adapted to receive a needle.

17. The suture package of claim 14 with at least one suture contained therein.

* * * * *